(12) United States Patent
Vogt

(10) Patent No.: US 10,509,003 B2
(45) Date of Patent: Dec. 17, 2019

(54) CONDUCTIVITY SENSOR AND METHOD FOR DETERMINING THE ELECTRICAL CONDUCTIVITY OF A LIQUID MEDIUM

(71) Applicant: KROHNE Messtechnik GmbH, Duisburg (DE)

(72) Inventor: Michael Vogt, Bochum (DE)

(73) Assignee: KROHNE MESSTECHNIK GMBH, Duisburg (DE)

( * ) Notice: Subject to any disclaimer, the term of this patent is extended or adjusted under 35 U.S.C. 154(b) by 208 days.

(21) Appl. No.: 15/783,175

(22) Filed: Oct. 13, 2017

(65) Prior Publication Data

US 2018/0106743 A1 Apr. 19, 2018

(30) Foreign Application Priority Data

Oct. 13, 2016 (DE) .................. 10 2016 119 508

(51) Int. Cl.
*G01N 27/07* (2006.01)
*G01R 27/22* (2006.01)
(Continued)

(52) U.S. Cl.
CPC ........... *G01N 27/07* (2013.01); *G01N 27/023* (2013.01); *G01N 27/025* (2013.01); *G01N 27/08* (2013.01); *G01R 27/22* (2013.01)

(58) Field of Classification Search
CPC ...... G01N 27/00; G01N 27/02; G01N 27/023; G01N 27/025; G01N 27/04; G01N 27/06; G01N 27/07; G01N 27/08; G01N 27/18; G01N 27/22; G01N 17/00; G01N 25/00; G01N 25/18; G01N 25/20; G01N 30/66; G01N 2030/345; G01N 2030/645; G01R 27/00; G01R 27/02; G01R 27/26; G01R 27/2611; G01R 27/267; G01R 27/22
(Continued)

(56) References Cited

U.S. PATENT DOCUMENTS 3,855,522 A * 12/1974 Kobayashi ........... G01N 27/023
324/445
3,924,175 A 12/1975 Wilson
(Continued)

FOREIGN PATENT DOCUMENTS

DE 43 07 379 C1 7/1994
DE 195 37 059 C2 9/1999
(Continued)

*Primary Examiner* — Hoai-An D. Nguyen
(74) *Attorney, Agent, or Firm* — David S. Safran; Roberts Mlotkowski Safran Cole & Calderon, P.C.

(57) ABSTRACT

A conductivity sensor for measuring the electrical conductivity of a liquid medium having at least a first coil, a current source and a control and evaluation unit, the current source being connected to the first coil. The conductivity sensor has the ability to determine a particularly large range of electric conductivity by at least a first electrode and a second electrode and at least one voltage measuring unit being provided, the voltage measuring unit being connected to the first electrode and the second electrode, the control and evaluation unit being connected to the current source and to the voltage measuring unit, and the first electrode and the second electrode being out of electrical contact with the first coil.

20 Claims, 12 Drawing Sheets

(51) Int. Cl.
*G01N 27/02* (2006.01)
*G01N 27/08* (2006.01)

(58) Field of Classification Search
USPC ........ 324/600, 649, 654, 691, 722, 425, 439
See application file for complete search history.

(56) References Cited

U.S. PATENT DOCUMENTS

| | | | |
|---|---|---|---|
| 4,810,963 | A | 3/1989 | Blake-Coleman et al. |
| 4,969,363 | A | 11/1990 | Mochizuki |
| 5,089,781 | A | 2/1992 | Arichika et al. |
| 5,225,783 | A | 7/1993 | Suzuki et al. |
| 6,812,709 | B2 | 11/2004 | Wieland et al. |
| 7,078,909 | B2 | 7/2006 | Feng et al. |
| 7,965,167 | B2 | 6/2011 | Völker et al. |
| 8,456,178 | B2 * | 6/2013 | Wang .................. G01N 27/023 324/654 |
| 8,736,287 | B2 * | 5/2014 | Dhirani ............ G01N 27/4473 204/403.01 |
| 2003/0197499 | A1 * | 10/2003 | Wieland ............ G01N 27/023 324/94 |
| 2004/0012395 | A1 | 1/2004 | Salamitou |
| 2007/0018659 | A1 | 1/2007 | Homan et al. |
| 2007/0042243 | A1 * | 2/2007 | Bai .................. H01M 8/04067 320/101 |
| 2008/0022763 | A1 * | 1/2008 | Maute .................. E21B 47/102 73/152.29 |
| 2011/0140716 | A1 * | 6/2011 | Wang .................. G01N 27/025 324/654 |
| 2012/0098549 | A1 * | 4/2012 | Wang .................. G01N 27/026 324/649 |
| 2012/0326711 | A1 * | 12/2012 | Roper ................ G01N 27/025 324/252 |
| 2016/0178788 | A1 * | 6/2016 | Zhang .................... G01V 3/28 324/324 |

FOREIGN PATENT DOCUMENTS

| | | |
|---|---|---|
| DE | 102 12 494 A1 | 10/2003 |
| DE | 10 2005 026 052 B3 | 3/2007 |
| DE | 10 2006 056 174 A1 | 5/2008 |
| JP | S 62-157559 A | 7/1987 |
| JP | H 9-329633 A | 12/1997 |
| WO | 85/04481 A1 | 10/1985 |

* cited by examiner

CONDUCTIVITY SENSOR AND METHOD FOR DETERMINING THE ELECTRICAL CONDUCTIVITY OF A LIQUID MEDIUM

BACKGROUND OF THE INVENTION

Field of the Invention

The invention is based on a conductivity sensor for measuring the electrical conductivity of a liquid medium.

Description of Related Art

Furthermore, the invention is based on a method for determining the electrical conductivity of a liquid medium.

Conductivity sensors are known from the prior art that determine the electrical conductivity of a liquid either inductively or conductively. The type of determination of the electrical conductivity depends, in particular, on the magnitude, i.e., the value of the conductivity to be expected. In principle, conductive conductivity sensors are suitable for the detection of small conductivities, whereas inductive conductivity sensors are preferably used for the determination of large conductivities.

The electrical conductivity of a medium is the reciprocal of the specific resistance. Thus, the electrical conductivity is determined by measuring the resistance of the medium to be examined.

Conductive conductivity sensors measure the electrical conductivity by detecting the ohmic resistance of the liquid using the current strength, the voltage drop and the geometry of the measuring arrangement. For this, conductive conductivity sensors typically have at least two electrodes, which are arranged in the medium to be measured, an electrical contact between the electrodes is produced only by the medium to be measured. An alternating voltage is applied to these electrodes to avoid or minimize polarization effects. To determine the resistance, the current flowing through the liquid and the voltage drop across the liquid are determined. Taking into account the geometry of the measuring arrangement, the specific resistance and the electrical conductivity of the liquid can then be determined.

A conductive conductivity sensor with two electrodes is known, for example, from the German Patent Application DE 102 12 494 A1, German Patent DE 195 37 059 C2 or from German Patent Application DE 196 43 967 A1.

A measuring arrangement with at least four electrodes is known, for example, from German Patent DE 2501812 C2 and corresponding U.S. Pat. No. 3,924,175, from German Patent DE 43 07 379 C1 as well as from German Patent Application DE 10 2005 026 052 B3.

In contrast to the above-described determination of the electrical conductivity, in which the electrodes are galvanically coupled to the medium to be measured, an inductive conductivity sensor is based on the induction of an eddy current in the medium by means of a first toroidal coil, the induced eddy current generates a magnetic field, which preferably induces a current in a second toroidal coil that is detected by measurement. The magnitude of the eddy current induced in the medium depends on the electrical conductivity of the medium, so that the current induced in the second toroidal coil (or the voltage induced there in the case of a high-resistance tapping) is a measure of the medium conductivity. The two coils form virtually the primary and secondary sides of a transformer, which are coupled via the electrical vortex field induced in the medium.

Inductive conductivity sensors are known, for example, from the German Patent DE 198 51 146 134 which corresponds to U.S. Pat. No. 6,812,709 B2, from German Patent Application DE 10 2006 025 194 A1 which corresponds to U.S. Pat. No. 7,965,167 B2 and from the German Patent Application DE 10 2006 056 174 A1.

U.S. Pat. No. 7,078,909 B2 discloses an inductive conductivity sensor comprising a transmitting coil and a receiving coil, the transmitting coil induces a current in the fluid to be measured, the induced current is guided into a conductor loop by means of electrodes that are in contact with the fluid, and the receiving coil inductively detects the current conducted by the conductor loop. Accordingly, the receiving coil is not arranged directly in the region of the pipeline through which the fluid flows. Alternatively, both the transmitting coil and the receiving coil can also be connected inductively to the conductor loop, whereby the current induced in the fluid is neither directly introduced by the transmitting coil nor detected directly by the receiving coil. This has the advantage that the size of the receiving coil and the size of the transmitting coil are independent of the diameter of the pipeline through which the fluid flows.

The conductivity sensors described above, however, have the disadvantage that they are designed either for the detection of high or of low conductivities—by principle.

SUMMARY OF THE INVENTION

Based on the prior art, the object of the invention is to provide a conductivity sensor and a method for determining the electrical conductivity of a liquid medium with which a particularly large value range of the electrical conductivity can be determined.

According to the invention, it has been recognized that a combination of the methods known from the prior art makes it possible to measure a particularly large range of values of the electrical conductivity, whereby in particular mean value ranges can be detected particularly well. In principle, there are two alternative measuring principles which are implemented according to the invention: According to the inductive-conductive measuring principle, a current flow is induced in the liquid medium and the current flow is detected by electrodes galvanically coupled to the liquid; for this, for example, the electrical potential difference between the electrodes caused by the current flow can be evaluated. According to the reverse conductive-inductive method, an electrical current is introduced into the liquid medium by means of electrodes that are electrically coupled, and the current is then detected inductively.

According to a first teaching of the present invention (inductive-conductive measuring principle), the above-stated object is achieved by a conductivity sensor for measuring the electrical conductivity of a liquid medium comprising at least a first coil, preferably a transmitting coil for generating a temporally varying magnetic field, a current source and a control and evaluation unit, the current source is connected to the first coil, in that at least a first electrode and a second electrode and at least a voltage measuring unit are provided, the voltage measuring unit is connected to the first electrode and the second electrode, the control and evaluation unit is connected to the current source and to the voltage measuring unit, and the first electrode and the second electrode are arranged in such a way that the first electrode and the second electrode have no electrical contact with the first coil.

In order to implement the above-described inductive-conductive measuring principle, the conductivity sensor has at least a first coil, preferably a transmitting coil, for generating a temporally changing magnetic field, an electric vortex field is induced in the liquid medium during operation by the first coil. In the case of a non-zero electrical conductivity, this results in a current flow with a current density $J_F$, which in turn causes a voltage drop across the current path in the liquid. In order to detect this voltage drop, a first and a second electrode are arranged in the range of the first coil, a preferably high-impedance voltage measuring unit is provided with which the voltage drop occurring at the two electrodes can be measured. In addition, the conductivity sensor according to the invention has a control and evaluation unit, which is designed in such a manner that it determines the electrical conductivity of the liquid medium from the values of the current and the voltage. In addition, the control and evaluation unit takes into account the geometry of the measurement arrangement for determining the electrical conductivity, the measuring arrangement comprises the arrangement or configuration of the first coil as well as of the first and second electrodes.

A high-impedance voltage measuring unit has the advantage that no substantial current flows through the first and the second electrode and no polarization effects that permanently interfere with measurement occur at the electrodes.

The conductivity sensor according to the invention is suitable both for measuring the conductivity of deionized water and for measuring the electrical conductivity of acids or alkalis.

To eliminate unwanted influences on the measurement of, e.g., parasitic circuit elements, such as the self-inductance of the coil, suitable approaches and methods can be implemented within the control and evaluation unit according to an advantageous design. In particular, the control and evaluation unit has a deposit of analytical circuit models and a complex evaluation in the case of time-harmonic variables. In addition, the control and evaluation unit can transmit calibration data, e.g., for a correction of systematic measurement errors, the calibration data are taken into account in the evaluation.

According to a second independent teaching (conductive-inductive measuring principle) the above object is achieved by a complementary use of the elements of a conductivity sensor. The object is accordingly achieved by a conductivity sensor for measuring the electrical conductivity of a liquid medium, comprising at least a first electrode and a second electrode, at least a current or voltage source and a control and evaluation unit, the current or voltage source is connected to the first electrode and second electrode in that additionally at least a first coil, preferably a receiving coil, and a current measuring unit are provided, the current measuring unit is connected to the first coil, the control and evaluation unit is connected to the current or voltage source and to the current measuring unit, and the first electrode and the second electrode are arranged such that the first electrode and the second electrode have no electrical contact with the first coil.

In order to implement the conductive-inductive measuring principle, a current or a voltage, in particular an alternating current or an alternating voltage and, in this respect, a temporally changing electric field, is introduced into the liquid medium during the operation of the conductivity sensor via the current or voltage source and via the first and the second electrode. The first coil is arranged such that a temporally changing magnetic flux density is induced in the first coil due to the temporally changing electric field, whereby, as a result, the current flow through the coil can be measured. Since the current flow depends on the electrical conductivity of the medium, the electrical conductivity of the medium can thus be inferred.

According to a first design of the conductivity sensors according to the invention, i.e., both the conductivity sensor according to the inductive-conductive measuring principle and the conductivity sensor according to the conductive-inductive measuring principle, the first coil is a toroidal coil, preferably with a ferromagnetic ring core.

According to a further advantageous design, the first and the second electrode are designed as ring electrodes.

Furthermore, according to an advantageous design, the first and the second electrode have an electrically conductive, metallic layer, the voltage drop across the liquid to be measured can be detected via the metallic layer or the current or the voltage can be introduced into the liquid via the metallic layer.

In addition, it is advantageous when an electrically insulating unit, preferably an electrically insulating tube, is provided, the electrically insulating unit has an interior space and an exterior space, the interior space is open, the first coil surrounds the electrically insulating unit, and the first coil and the first and second electrodes are preferably arranged parallel to one another along the electrically insulating unit. The electrically insulating unit is designed in such a manner that, during operation of the conductivity sensor, the medium to be measured is arranged within the electrically insulating unit so that an electric field can be established in the medium.

An open interior can be implemented, for example, in that the electrically insulating unit is tube-shaped, i.e., is designed with free cross section. Alternatively, the electrically insulating unit can also have a different shape. It is only relevant that the electrically insulating unit has at least one opening through which the medium can enter and exit the electrically insulating unit during operation.

It is particularly advantageous when the first and the second electrode are arranged in the inner space and, in particular, on the inner side of the electrically insulating unit.

According to a further advantageous design, the first coil is arranged between the first and the second electrode. This design is advantageous in that, during operation of the sensor, the electric field generated in the liquid medium by induction or by applying a potential difference is formed, in particular, in the region of the first coil and, if the first coil is a toroidal coil with a ring core, in the region of the ring core.

It is particularly advantageous when the first electrode and the second electrode are arranged at the ends of the electrically insulating unit. The first and second electrodes then have a maximum distance from one another. If the electrically insulating unit is an electrically insulating tube and the first and the second electrode are designed as ring electrodes, the first and second electrodes preferably have the same internal and external diameter as the electrically insulating tube. Particularly preferably, the first and second electrodes are integrated in the electrically insulating tube. This has the advantage that the first and the second electrode can be constructed in a simple manner and, furthermore, a good seal between the first and second electrodes and the electrically insulating tube is particularly easy to implement.

Alternatively, the first electrode and the second electrode may be arranged on the same side of the first coil. This arrangement is advantageous in view of a good electrical decoupling of the first and second electrodes from the first coil. This arrangement causes, in particular, the suppression of unwanted couplings by way of stray magnetic fields of the first coil, for example by electric fields between the windings of the first coil.

In order to avoid undesired couplings between the first coil and the first and/or the second electrode, it is also advantageous when at least one side of the first coil is provided with a shield, in particular an electrically conductive and/or ferromagnetic plate or an electrically conductive and/or ferromagnetic sheet foil.

According to a particularly preferred design, at least a second coil is provided, the second coil being connected in parallel or in series to the first coil or having no connection with the first coil.

In this case, the first and the second coil can have the same number of turns, but alternatively the number of turns of the second coil can also deviate from the number of turns of the first coil.

According to this design, the measurement concept of the inductive-conductive or the conductive-inductive measurement can advantageously be combined with a further conductive and/or inductive measurement of the electrical conductivity in order to enable a self-monitoring function which is particularly relevant in the context of the NAMUR recommendation NE 107 "Self-monitoring and diagnosis of field devices". Furthermore, this embodiment makes possible a variation in the geometry of the measuring arrangement, which is also taken into account in the determination of the conductivity by the control and evaluation unit. With regard to an exact configuration of the self-monitoring function and a possible variation of the geometry of the measuring arrangement, reference is made to the corresponding description of the method according to the invention.

It is also advantageous when the conductivity sensor according to a further design has a housing, at least the first coil and the first and the second electrode are arranged within the housing. The housing protects the components arranged in the housing during operation from the liquid medium surrounding the conductivity sensor. It is particularly advantageous when the housing simultaneously has at least one shield for avoiding a coupling between the first coil and the first and/or the second electrode. The housing with the preferably provided shield is configured in such a manner that a magnetic flux surrounding the electrically insulating unit and a free current path for the induced eddy currents can be produced, the current path leads through the electrically insulating unit filled with the liquid medium and further through the outer region of the electrically insulating unit.

According to a further design, the conductivity sensor is configured in such a manner that, during operation, the conductivity sensor carries out one of the methods described in the following.

According to a third teaching of the present invention, the object mentioned at the outset is achieved by a method for determining the electrical conductivity of a liquid medium by means of a conductivity sensor arranged in the liquid medium, the conductivity sensor comprises at least a first coil, preferably a transmitting coil, a current source and a control and evaluation unit, the current source is connected to the first coil, in that at least a first electrode and a second electrode and a voltage measuring unit are additionally provided, the voltage measuring unit is connected to the first electrode and the second electrode, and the control and evaluation unit is connected to the current source and to the voltage measuring unit, the first electrode and the second electrode have no electrical contact with the first coil, and the first electrode and the second electrode are in contact with the first electrode and the second electrode via the liquid medium, and that the method comprises the following steps:

a. Generating an alternating current in the first coil by means of the current source, whereby the first coil generates a temporally changing magnetic flux density which induces an electric field in the liquid medium,
b. measuring the voltage between the first electrode and the second electrode by the voltage measuring unit,
c. transferring the values of the voltage and the current to the control and evaluation unit,
d. determining the electrical conductivity from the values of the voltage and the current by the control and evaluation unit.

Additionally, the object mentioned at the outset is achieved according to a fourth teaching of the present invention by a method for determining the electrical conductivity of a liquid medium by means of a conductivity sensor arranged in the liquid medium, the conductivity sensor comprises at least a first electrode and a second electrode, at least a current or voltage source and a control and evaluation unit, the current or voltage source is connected to the first electrode and the second electrode, in that at least one first coil and a current measuring unit are additionally provided, the current measuring unit is connected to the first coil, the control and evaluation unit is connected to the current or voltage source and to the current measuring unit, and the first electrode and the second electrode are arranged in such a manner that the first electrode and the second electrode have no electrical contact with the first coil, the first electrode and the second electrode are in contact with one another via the liquid medium, and that the method comprises the following steps:

a. Applying an alternating voltage or an alternating current to the first electrode and the second electrode by the current or voltage source, whereby a temporally changing electric field is introduced into the liquid medium, whereby a temporally changing magnetic flux density is induced in the first coil,
b. measuring the current flowing through the first coil by the current measuring unit,
c. transmitting the values of the voltage and the measured current to the control and evaluation unit, and
d. determining the electrical conductivity from the values of the voltage and the current by the control and evaluation unit.

Like the conductivity sensors according to the invention, the methods according to the invention have the advantage that by combining the inductive or conductive coupling of the temporally changing electric field into the liquid medium and the conductive or inductive detection of the electric field, a particularly large range of values of the electrical conductivity can be measured, the methods according to the invention are particularly suitable for the verification of mean values of the conductivity.

The alternating current applied to the first coil or to the first and second electrodes or the alternating voltage applied to the first and the second electrodes preferably has a time-harmonic course, alternatively other courses over time are also conceivable.

According to an advantageous implementation, the conductivity sensor has at least a second coil, the second coil has no connection with the first coil or is connected in parallel or in series with the first coil, and the determination of the electrical conductivity is carried out both by means of the first coil and by means of the second coil, preferably using the combination of the first coil and the second coil.

Thereby, the first and the second coil can have the same number of turns, but alternatively the number of turns of the second coil can also deviate from the number of turns of the first coil.

For example, a first electric field is initially induced in the medium by means of the first coil, and the electrical conductivity is determined based on the first electric field, and a second electric field is subsequently induced in the medium by means of the second coil, and the electrical conductivity is also determined based on the second electric field. The two coils can thereby have the same alternating current flowing through them, alternatively, the alternating current flowing through the second coil can deviate in its amplitude and/or its phase and/or its frequency from the alternating current flowing through the first coil.

Alternatively, an electric field can be introduced into the liquid by means of the first and the second electrode, the electric field is first detected inductively by way of the first coil, and then by way of the second coil.

Alternatively, it is conceivable that, after or during the determination of the electrical conductivity by means of the inductive-conductive method or after the determination of the electrical conductivity by means of the conductive-inductive method, the first coil induces an electric field in the liquid medium, which is inductively detected by the second coil.

As an alternative to the inductive-conductive or the conductive-inductive determination, the electrical conductivity, the conductivity can additionally be determined purely conductively by means of the first and the second electrode.

If the second coil is connected in parallel or in series to the first coil, the coils simultaneously generate an electric field which preferably superimposes itself. According to this implementation, the measuring effect can be further intensified.

Overall, the redundant determination of the electrical conductivity makes it possible, on the one hand, to detect error sources early in the course of self-monitoring, and, on the other hand, makes it possible to vary the measuring arrangement, whereby the accuracy and reliability of the determination of the conductivity can be increased. In particular, depending on the type of combination of the individual methods, individual components of the conductivity sensor can be verified.

It is particularly preferred that the method is carried out using one of the illustrated conductivity sensors. In particular, all described implementations of the conductivity sensors are suitable for the combination with the method according to the invention.

In detail, there is a plurality of possibilities for designing and further developing the conductivity sensor according to the invention and the method according to the invention. For this, reference is the following description of preferred embodiments in conjunction with the accompanying drawings.

DETAILED DESCRIPTION OF THE INVENTION

Figure 1:
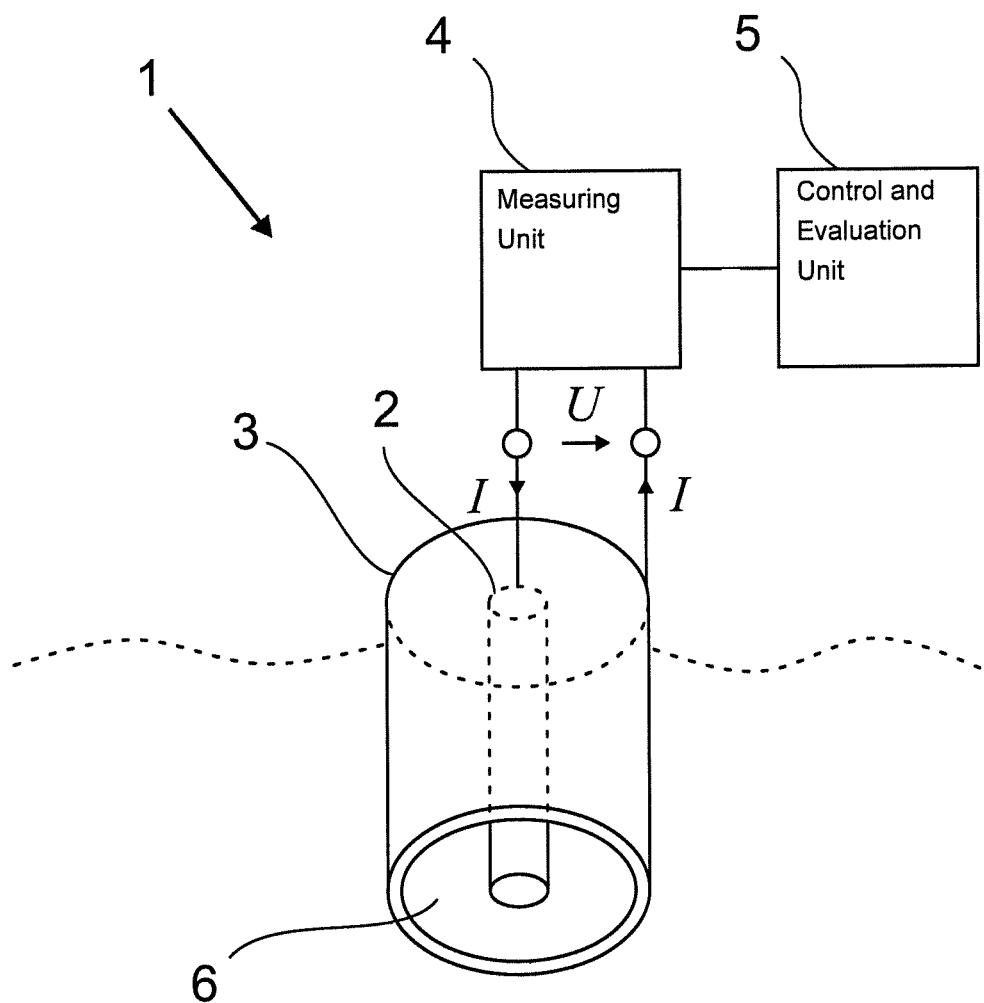
FIG. 1 shows a first conductive conductivity sensor from the prior art.

FIG. 1 schematically shows a conductive conductivity sensor 1 from the prior art. The conductivity sensor 1 has a first electrode 2 and a second electrode 3 as well as a current or voltage source with a current and/or voltage measuring unit 4. In addition, the conductivity sensor 1 comprises a control and evaluation unit 5, which is connected to the current and voltage source with a current and/or voltage measuring unit 4. During operation, the conductivity sensor 1 for measuring the electrical conductivity κ of a liquid 6 is immersed in the liquid 6.

In order to determine the conductivity κ, an alternating current I or an alternating voltage U is applied by the current or voltage source 4 to the first electrode 2 and to the second electrode 3, and the current I flowing through the liquid 6 and the voltage drop U present across the liquid 6 are detected by the current and/or voltage measuring unit 4. The admittance $Y_m = I/U$, i.e., the ratio of the alternating current to the voltage applied to the electrodes, is determined in the control and evaluation unit 5 using the measured values of the current I and the voltage U. Neglecting possible polarization effects at the electrodes, the admittance $Y_m$ can be expressed in real and imaginary part as follows:

$$Y_{m,ideal} = \frac{I}{U} = G_m + jB_m \text{ with } G_m = \text{Re}\{Y_m\} = \frac{\kappa}{k_{zell,kond}} \propto \frac{1}{R_F}$$

where $G_m$ is the conductance, $B_m$ is the electric reactance (susceptance), κ is the electrical conductivity, $k_{zell,kond}$ is the cell constant of the measuring arrangement, and $R_F$ is the ohmic resistance of the current path. The cell constant $k_{zell,kond}$ is dependent on the geometry of the measuring arrangement, in particular the area and the distance of the electrodes. However, in the application of such a conductivity sensor 1, the polarization effects at the electrodes are generally not negligible, which results in additional parasitic effects and necessitates the inclusion of complicated models for the evaluation of the measurements.

Figure 2:
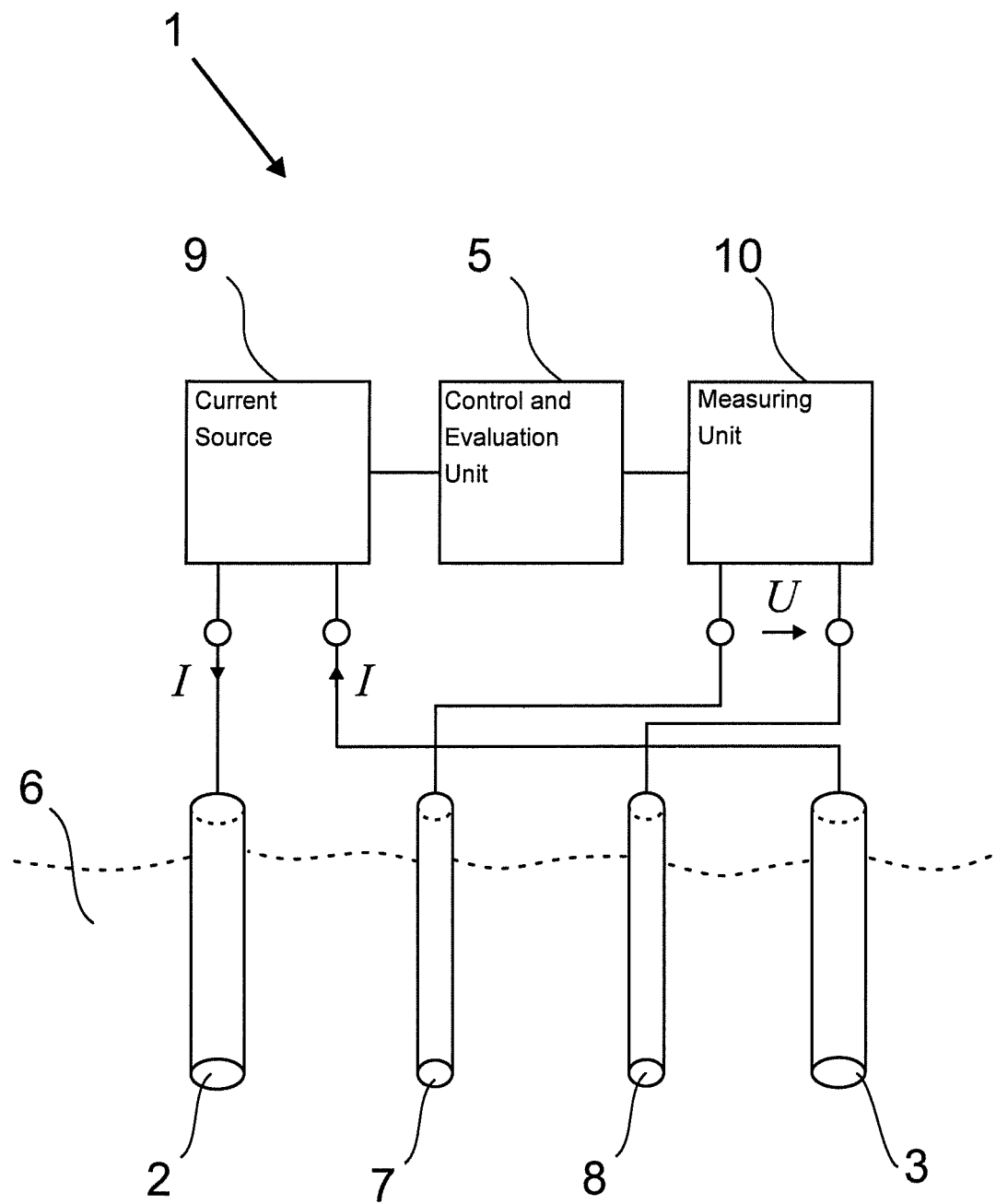
FIG. 2 shows a second conductive conductivity sensor from the prior art.

FIG. 2 also shows a conductivity sensor 1 from the prior art, the conductivity sensor 1 has four electrodes 2, 3, 7, 8, which are immersed in the liquid 6 to be measured during operation. In addition, the conductivity sensor 1 has a current source 9, a high-impedance voltage measuring unit 10 and a control and evaluation unit 5.

During operation of the illustrated conductivity sensor 1, an alternating current is introduced into the liquid 6 via the external electrodes 2, 3 with the help of the current source 9. A voltage drop across the liquid 6 is tapped with the two internal electrodes 7, 8 and with the help of the high-impedance voltage measuring unit 10. Due to the high-impedance tapping, no substantial current flows through the two internal measuring electrodes 7, 8, whereby no polarization effects interfering with the measurement occur at these two electrodes. As already described above, the control and evaluation unit 5 determines the electrical conductivity κ from the admittance $Y_m$ in dependence on the values of the current and the voltage.

Figure 3:
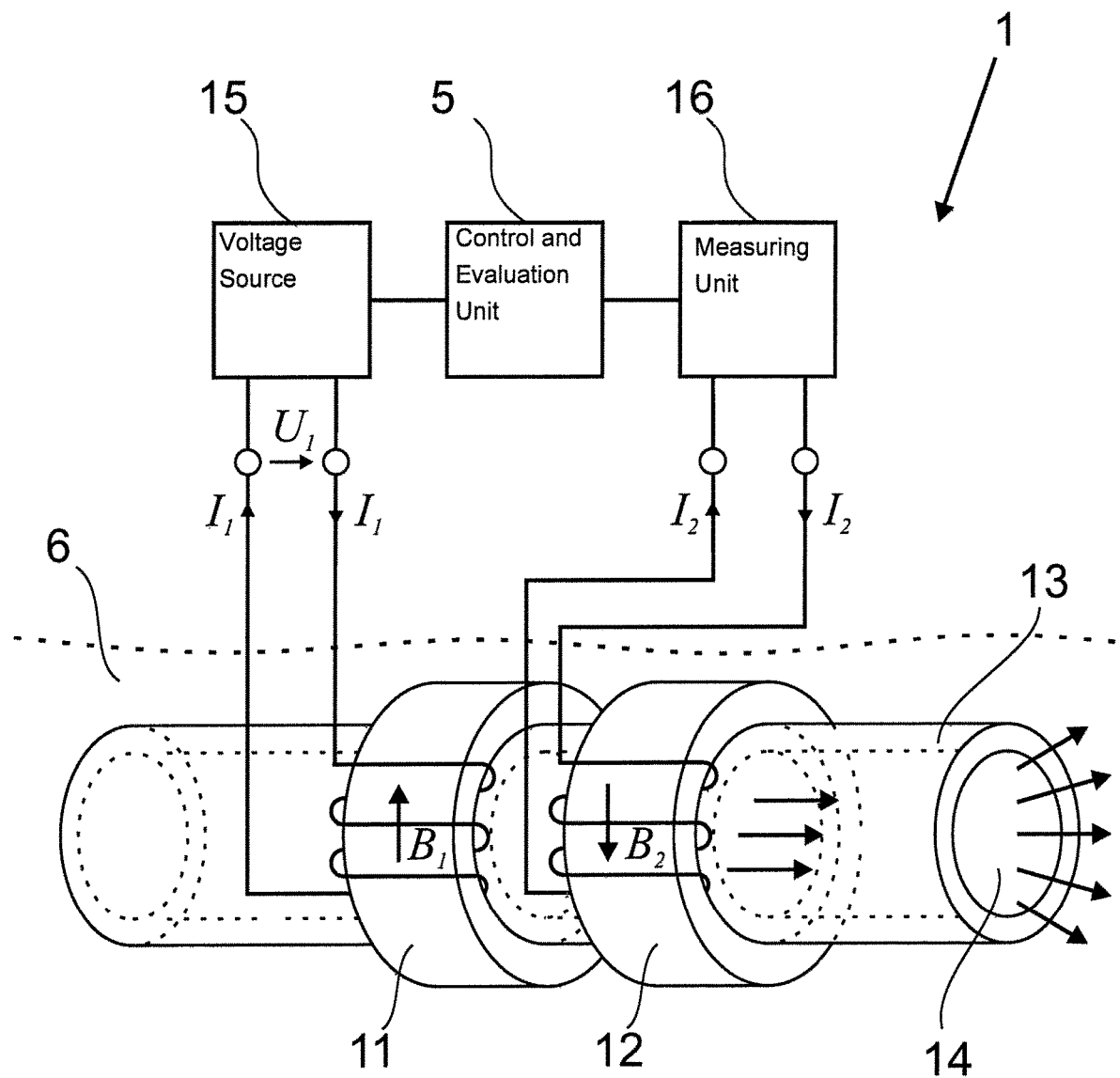
FIG. 3 shows a first inductive conductivity sensor from the prior art.

FIG. 3 shows an inductive conductivity sensor 1 from the prior art, the inductive conductivity sensor 1 has a first coil 11, here a transmitting coil in the form of a toroidal coil, and a second coil 12 as a receiving coil, likewise in the form of a toroidal coil. In addition, the conductivity sensor 1 has an electrically insulating tube 13 with a free tube cross section 14, the first coil 11 and the second coil 12 are arranged parallel to one another around the electrically insulating tube 13. During operation, the electrically insulating tube 13 together with the first coil 11 and the second coil 12 is arranged in a liquid 6 such that the liquid 6 is located within the electrically insulating tube 13. The first coil 11 is further connected to a voltage source 15 and the second coil 12 is connected to a low-impedance current measuring unit 16. Furthermore, a control and evaluation unit 5 is provided, which is connected to the voltage source 15 and the current measuring unit 16. During operation, an alternating magnetic flux density $B_1$ is generated by applying an alternating voltage to the first coil 11, whereby an eddy current with the current density $J_F$ is induced in the liquid 6. This flowing eddy current is detected inductively by the second coil 12. That means, the eddy current flowing in the liquid 6 generates a changing magnetic flux density $B_2$ in the second coil 12 so that a current flowing through the second coil 16 can subsequently be measured by the current measuring unit 16. The electrical conductivity κ is then determined using the measured admittance $Y_m$ in the control and evaluation unit 5, as already explained.

The admittance $Y_m$ has the following relation in the illustrated example:

$$Y_m = \frac{I_2}{U_1} = G_m + jB_m,$$

$$G_m = \text{Re}\{Y_m\} = \frac{1}{N_1 \cdot N_2 \cdot R_F} = \frac{\kappa}{k_{zell,ind,2coils}} \text{ with } R_F \propto \frac{1}{\kappa}$$

and $k_{zell,ind,2coils}$ is proportional to $N_1 \cdot N_2$ and $N_1$ is the number of turns of the first coil and $N_2$ is the number of turns of the second coil.

Figure 4:
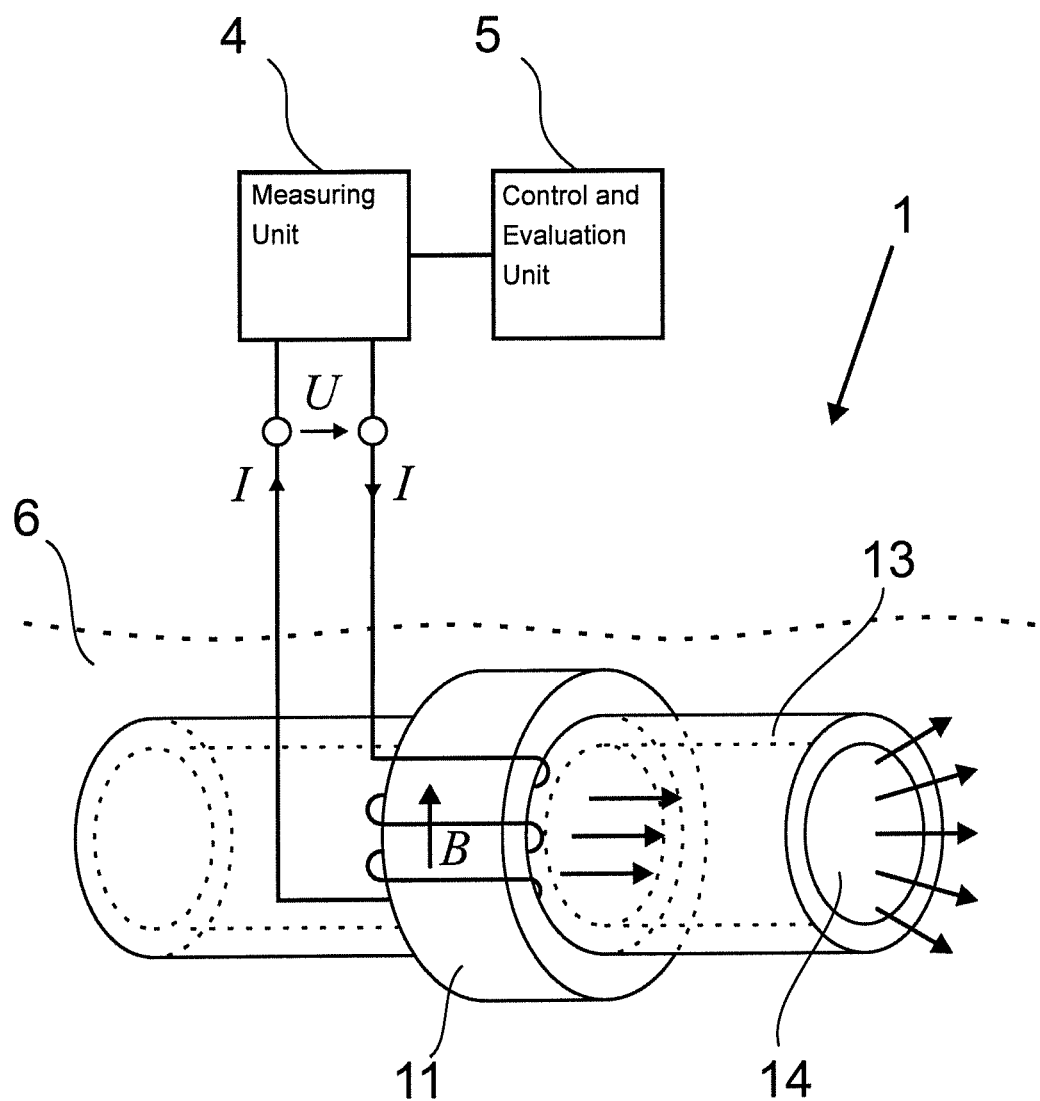
FIG. 4 shows a second inductive conductivity sensor from the prior art.

FIG. 4 also shows an inductive conductivity sensor 1 from the prior art, the illustrated conductivity sensor 1 has only a first coil 11. This coil 11 is arranged around an electrically insulating tube 13 with a free tube cross section 14, which is immersed in a liquid 6 during operation. In addition, a current or voltage source with current and/or voltage measuring unit 4 as well as a control and evaluation unit 5, which is connected to the current or voltage source with current and voltage measuring unit 4, are also shown.

Since only one coil 11 is present, the measuring concept now consists in measuring the input impedance at the connection terminals of coil 11, for which the current or voltage source with current and/or voltage measuring unit 4 is used.

As already stated above, the control and evaluation unit 5 determines the admittance $Y_m$, for which the following correlations hold true:

$$Y_m = \frac{I}{U} = \frac{1}{N^2} \cdot \left( \frac{1}{R_F} + \frac{N^2}{j\omega L} \right) = G_m + jB_m \text{ with } R_F \propto \frac{1}{\kappa},$$

N is the number of turns of the coil 11 and L is the self-inductance of the coil 11.

Thus, as above:

$$G_m = \text{Re}\{Y_m\} = \frac{1}{N^2 \cdot R_F} = \frac{\kappa}{k_{zell,ind,1coil}},$$

the cell constant $k_{zell,ind,1coil}$ is proportional to $N^2$.

Figure 5:
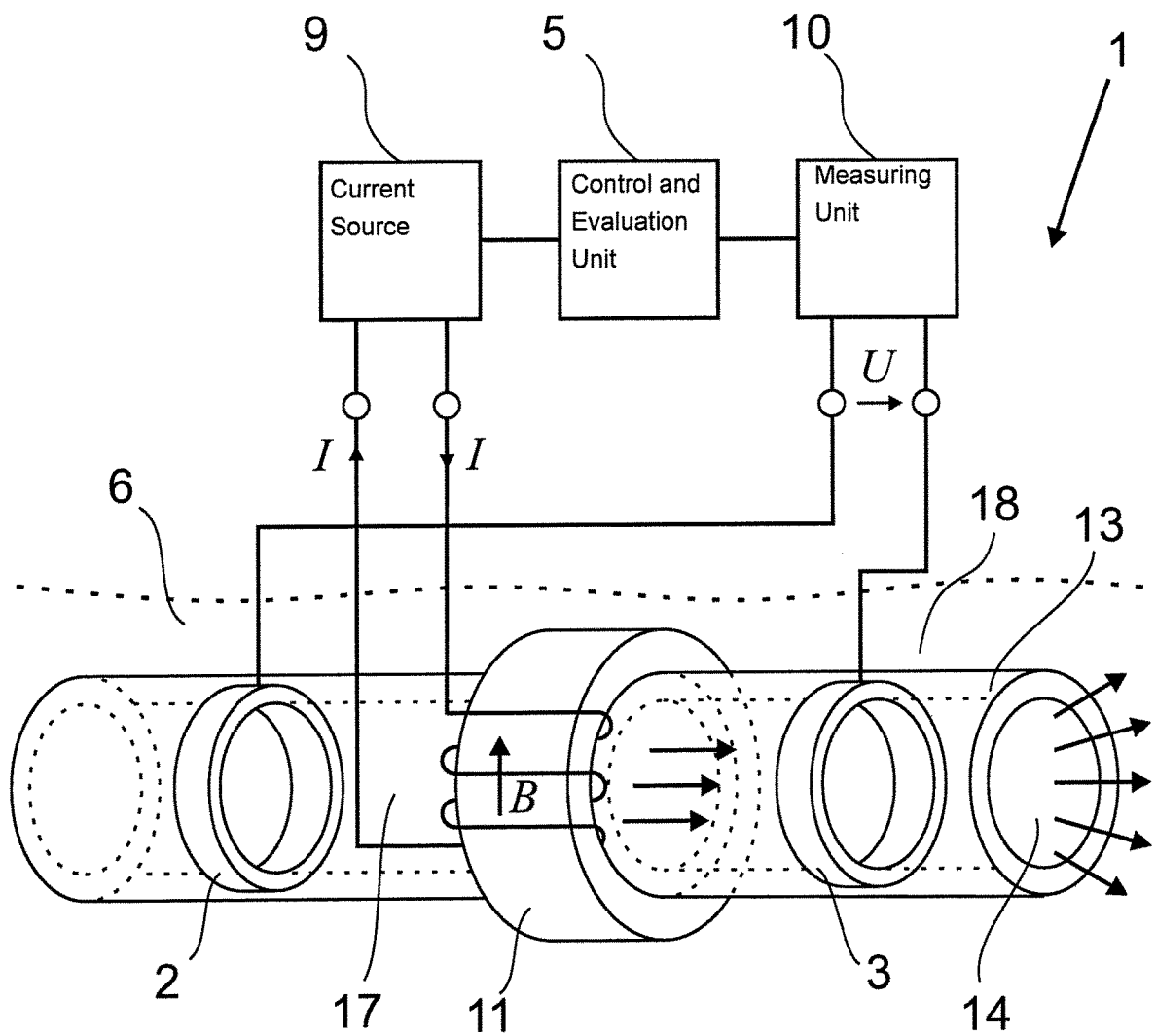
FIG. 5 shows a first embodiment of a conductivity sensor according to the invention.

FIG. 5 shows a first embodiment of a conductivity sensor 1 according to the invention, the conductivity sensor 1 determines the electrical conductivity κ of the liquid 6 during operation based on an inductive-conductive measuring principle. The illustrated conductivity sensor 1 comprises a first coil 11 as a transmitting coil in the form of a toroidal coil, a first electrode 2 and a second electrode 3, and an electrically insulating tube 13 with a free tube cross section 14, which is filled with the liquid 6 to be measured and is surrounded by the liquid 6. In addition, the electrically insulating tube 13 is surrounded by the first coil 11. The electrically insulating tube 13 also has an inner space 17 and an outer space 18. The first measuring electrode 2 and the second measuring electrode 3 are mounted in the inner space 17 on the inside of the electrically insulating tube 13, the first measuring electrode 2 and the second measuring electrode 3 are designed as metallic ring electrodes.

In addition, a current source 9 is provided, the current source 9 is connected to the first coil 11, an alternating current is applied to the first coil 11 during operation. The alternating current flowing through the first coil 11 causes a temporally changing magnetic flux density B in the region of the first coil 11, the temporally changing magnetic flux density B generates a temporally changing electric field $E_F$ within the liquid 6. In the event of a non-zero electrical conductivity κ of the liquid 6, this results in an electric current flow in the form of an eddy current with a current density $J_F$ along a closed current path, which is formed by the free tube cross section 14 and by the region filled with liquid 6 of the outer space 18 of the electrically insulating tube 13. Associated with the current density $J_F$, an electric field $E_F$ results within the liquid 6, which leads to a temporally changing electrical voltage drop U between the first electrode 2 and the second electrode 3. The voltage U applied between the first electrode 2 and the second electrode 3 is tapped using a high-ohmic voltage measuring unit 10 and is detected by measurement.

A control and evaluation unit 5 is connected to the current source 9 and the voltage measuring unit 10. The control and evaluation unit 5 is designed in such a manner that, during operation, it determines the electrical conductivity κ from the variables current I and voltage U, the temporal courses of the two variables are evaluated, in the case of time-harmonic variables, in particular their amplitudes and phases. In order to eliminate unwanted influences of e.g. parasitic circuit elements, such as the self-inductance of the coil or magnetic losses in the ring core, suitable approaches and methods can be implemented within the control and evaluation unit 5. In addition, calibration data are stored in the control and evaluation unit 5, e.g. for a correction of systematic measurement errors, which are included in the evaluation.

Figure 6:
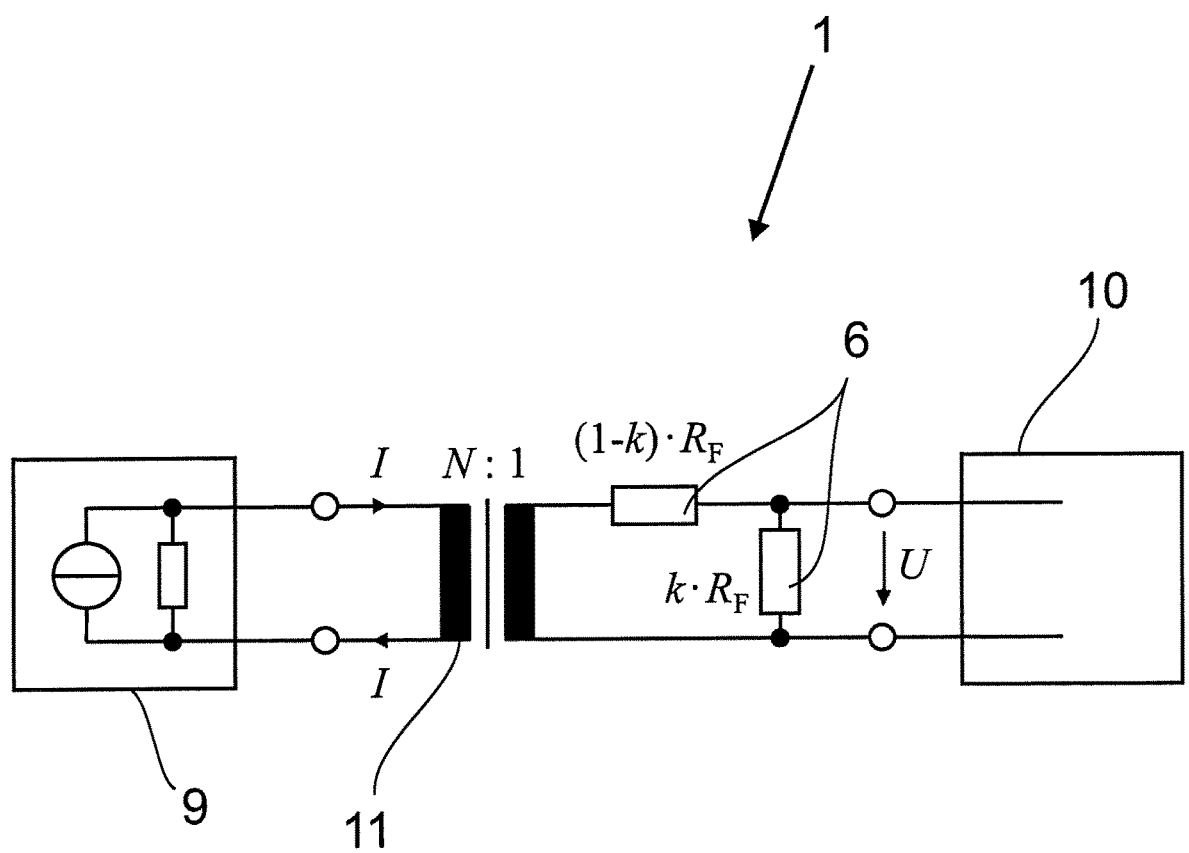
FIG. 6 is a first electrical equivalent circuit diagram.

FIG. 6 shows an electrical equivalent circuit diagram of the functional principle of an inductive-conductive conductivity sensor 1, as is shown, for example, in FIG. 5. A transformer is shown, the primary side is represented by the first coil 11 having the number of windings N and the secondary side having the number of windings 1, through the closed current path through the liquid 6. The ohmic resistance $R_F$ of the current path is divided into a first partial resistance of $k \cdot R_F$ with $0<k<1$ along the current path between the first electrode 2 and the second electrode 3 via the outer space 18 of the electrically insulating tube 13 and into a second partial resistance $(1-k) \cdot R_F$ between the first electrode 2 and the second electrode 3 along the current path in the inner space 17 of the electrically insulating tube 13. The current I and the voltage U are measured in the measuring arrangement according to FIG. 6, and the electrical conductivity κ is determined from the admittance $Y_m$ in the control and evaluation unit 5.

With regard to the following relationship between the secondary-side voltage U and the primary-side current I, reference is also made to the illustration in FIG. 6.

$$Y_m = \frac{I}{U} = \frac{1}{k \cdot N} \cdot \left( \frac{1}{R_F} + \frac{N^2}{j\omega L} \right) = G_m + jB_m \text{ with } R_F \propto \frac{1}{\kappa}.$$

In order to make the measurement of the electrical conductivity κ of the liquid 6 independent of the self-inductance L of the coil 11, $Y_m$ can advantageously be separately recorded and evaluated by real and imaginary part:

$$G_m = \text{Re}\{Y_m\} = \frac{1}{k \cdot N \cdot R_F} = \frac{\kappa}{k_{zell, indkond}}$$

Thereby, $k_{zell,indkond}$~N is the cell constant of the inductive-conductive conductivity sensor 1, $k_{zell,indkond}$ is dependent on the number of windings N of the first coil 11 and the geometry of the conductivity sensor 1.

As a result, a current in the form of an eddy current is inductively impressed into the liquid 6, and the resulting voltage drop between the first measuring electrode 2 and the second measuring electrode 3 is tapped galvanically coupled.

Figure 7:
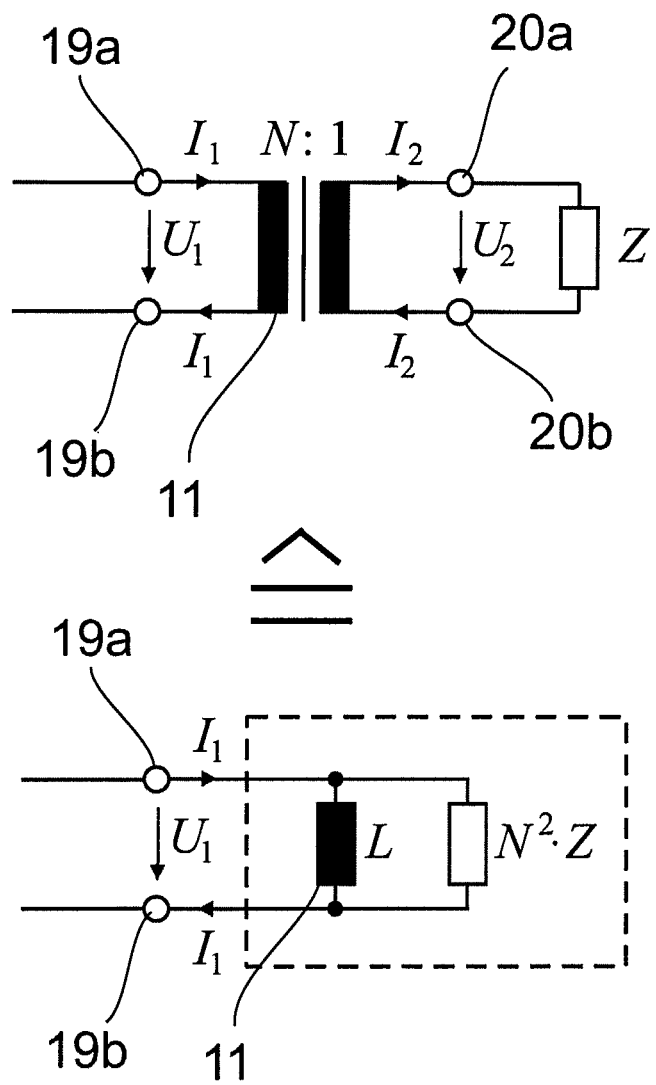
FIG. 7 is a second electrical equivalent circuit diagram.

FIG. 7 shows an electrical equivalent circuit diagram for the transformer formed by the first coil 11 having the self-inductance L and the number of windings N and by the closed current path through the liquid 6, an ideal, loss-free coupling is presumed in the illustration. $U_1$ and $I_1$ denote the voltage or the current at the primary side and $U_2$ and $I_2$ denote the voltage and the current at the secondary side. The voltage $U_1$ at the primary side is tapped with a pair of terminals 19a, 19b, and the voltage $U_2$ at the secondary side is tapped with a pair of terminals 20a, 20b. The illustration shows the general case in that the secondary side is terminated with the terminal pair 20a and 20b having a terminating impedance Z.

The input impedance $Z_{E1}$ in the primary side (pair of terminals 19a, 19b) results as illustrated in the following:

$$Z_{E1} = \frac{U_1}{I_1} = \frac{1}{\frac{1}{j\omega L} + \frac{1}{N^2 \cdot Z}},$$

ω is the angular frequency of the applied alternating current. Furthermore, $$U_2 = \frac{U_1}{N}$$

generally applies for the transformer.

If the above-described relationships are taken into account in the determination of the admittance $Y_m$ of the measuring arrangement shown in FIG. 6, the relationships described in respect to FIG. 6 are obtained.

Figure 8:
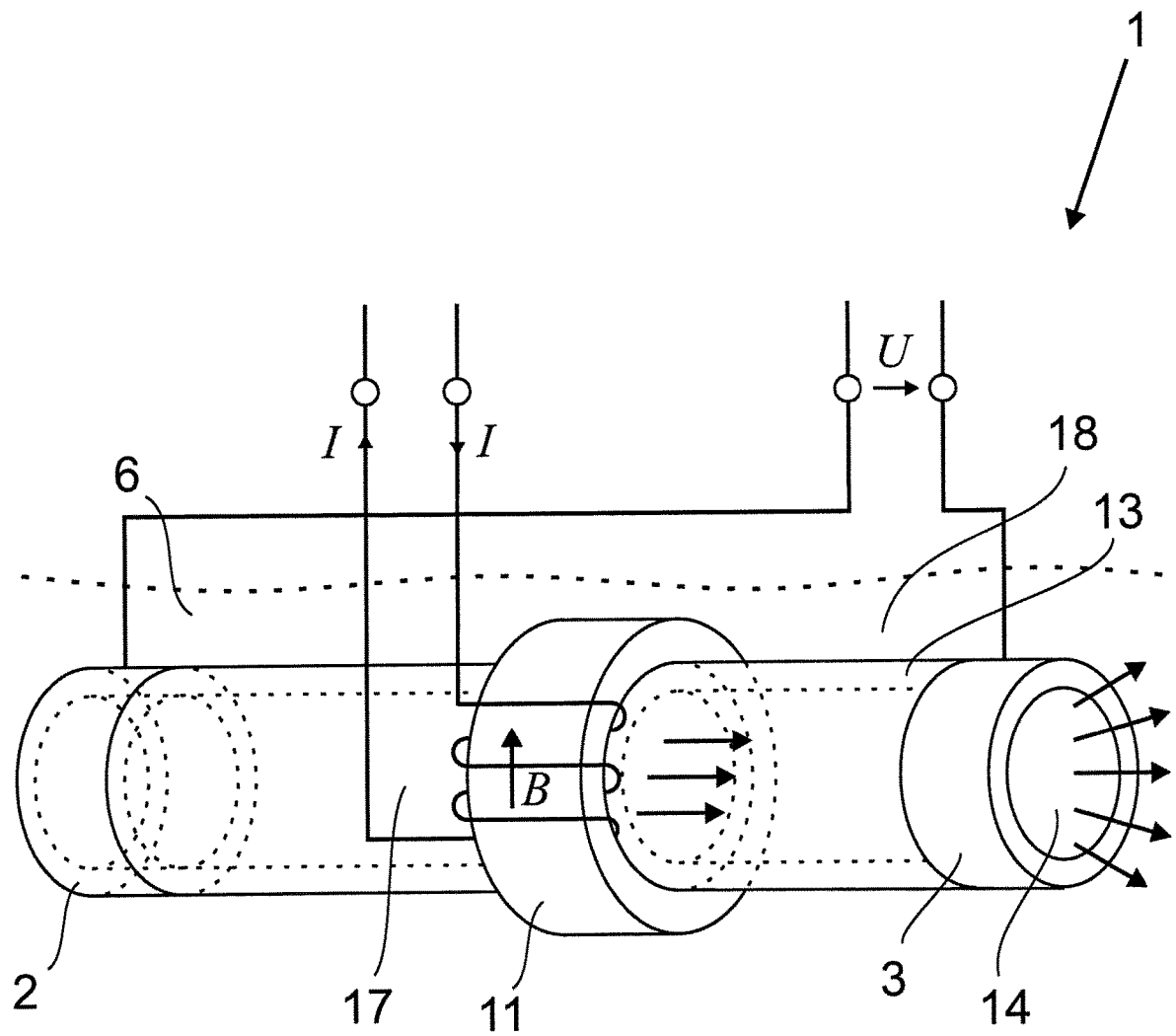
FIG. 8 shows a second embodiment of a conductivity sensor according to the invention.

FIG. 8 shows a second embodiment of a conductivity sensor 1 according to the invention, wherein, in contrast to the first embodiment shown in FIG. 5, the first electrode 2 and the second electrode 3 are arranged at the ends of the electrically insulating tube 13. The metallic surfaces of the first electrode 2 and the second electrode are in galvanic contact with the liquid 6 both in the inner space 17 of the electrically insulating tube 13 and in the outer space 18 of the electrically insulating tube.

The first electrode 2 and the second electrode 3 thereby have the same internal and external diameter as the electrically insulating tube 13.

Figure 9:
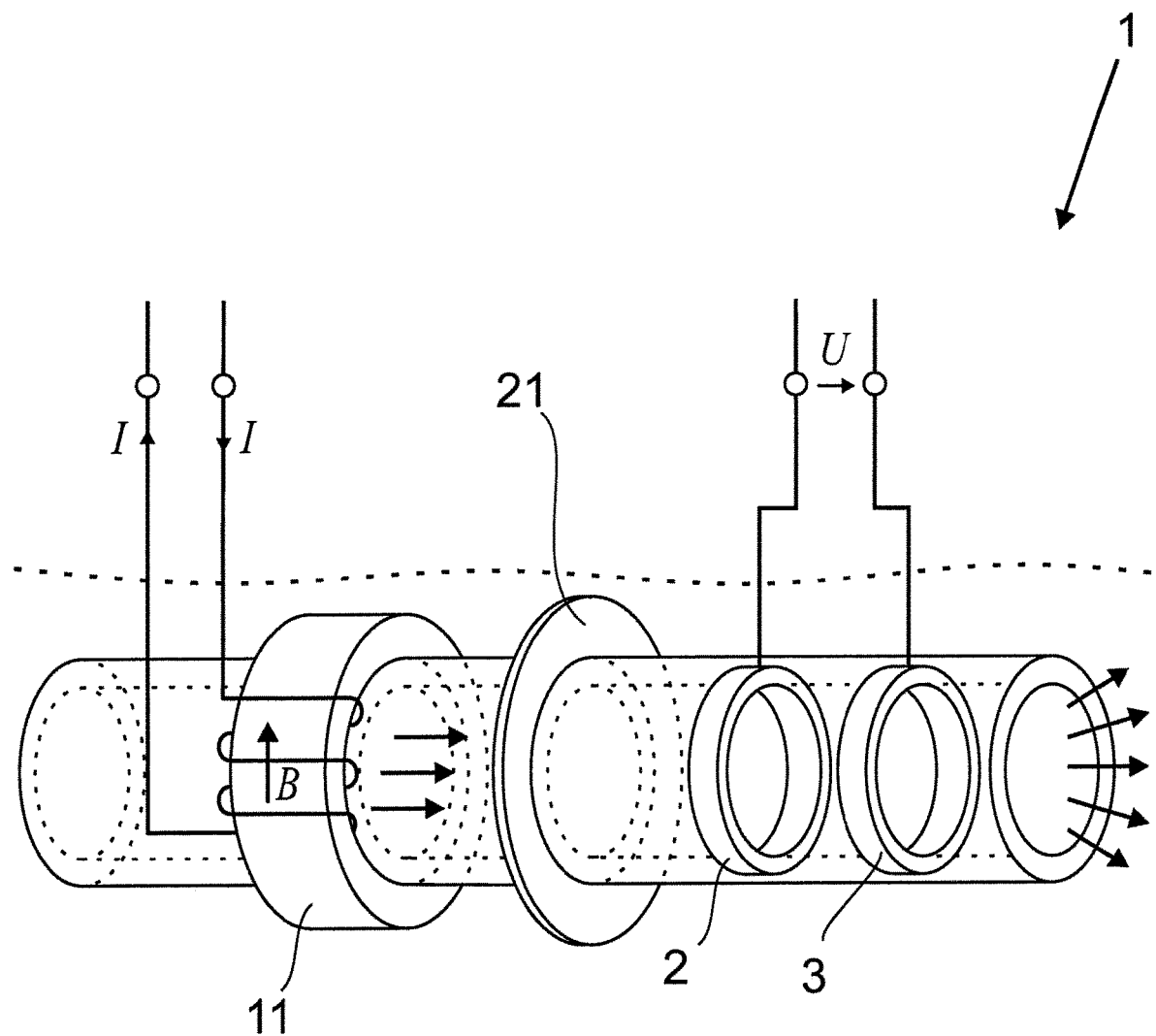
FIG. 9 shows a third embodiment of a conductivity sensor according to the invention.

FIG. 9 shows a third embodiment of a conductivity sensor 1 according to the invention, which implements an inductive-conductive measuring principle. According to the embodiment shown, the first electrode 2 and the second electrode 3 are arranged on the same side of the first coil 11. This is advantageous in view of a good electrical decoupling of the first electrode 2 and of the second electrode 3 from the first coil 11, in particular for suppressing undesirable couplings via stray magnetic fields of the first coil 11 through electric fields between the windings of the first coil 11.

In order to further avoid unwanted couplings, a shield 21 in the form of an electrically conductive plate is provided between the first coil 11 and the first electrode 2 and the second electrode 3.

Figure 10:
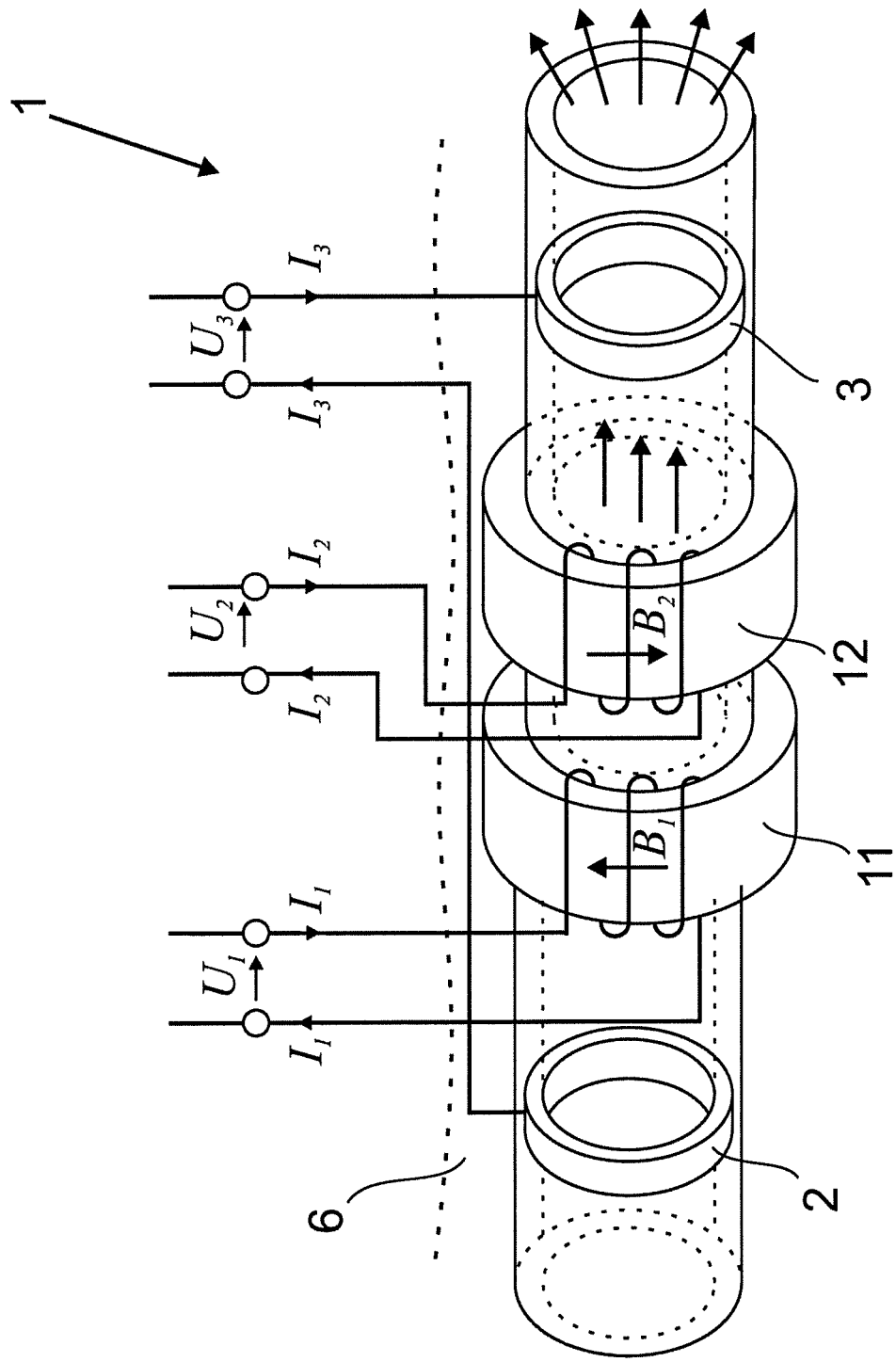
FIG. 10 shows a fourth embodiment of a conductivity sensor according to the invention.

FIG. 10 shows a fourth embodiment of a conductivity sensor 1 according to the invention, wherein, in addition to the first coil 11, a second coil 12 is provided, which can be used both as a transmitting coil and as a receiving coil. This embodiment has the advantage that the inductive-conductive measuring method can be coupled, for example, with an additional inductive-conductive measurement, the second coil 12 operates as a transmitting coil or with an additional inductive measurement, the second coil 12 detects the current impressed in the liquid 6 by the first coil 11. A multiple detection of the electrical conductivity κ has the advantage that the conductivity sensor 1 has an integrated self-monitoring function.

Figure 11:
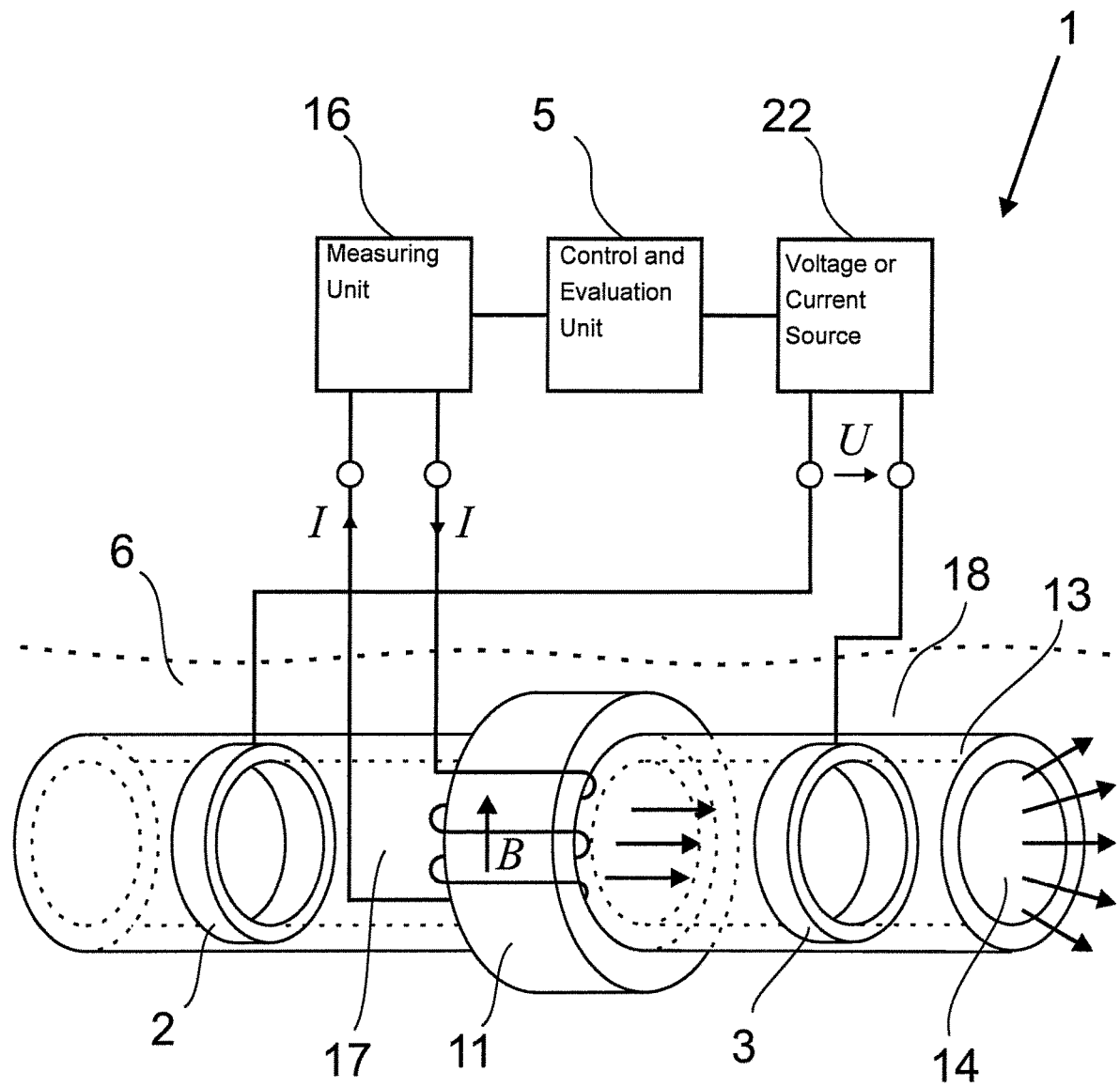
FIG. 11 shows a fifth embodiment of a conductivity sensor according to the invention.

FIG. 11 shows a fifth embodiment of a conductivity sensor 1 according to the invention, comprising a first coil 11, which is used here as a receiving coil, a first electrode 2 and a second electrode 3, the first coil 11 surrounds an electrically insulating tube 13, and first electrode 2 and the second electrode 3 are arranged on the inner side of the tube. The first electrode 2 and the second electrode 3 are connected to a voltage or current source 22. The first coil 11 is connected to a current measuring unit 16. Both the voltage or current source 22 and the current measuring unit 16 are connected to a control and evaluation unit 5. In the illustration, the electrically insulating tube 13 is immersed in the liquid 6 to be measured.

During operation, an alternating voltage or an alternating current is applied to the first electrode 2 and to the second electrode 3, whereby a changing electric field is formed in the liquid 6. This temporally changing electric field produces a magnetic flux density B in the first coil 11, whereby a current through the first coil 11 can be measured. The control and evaluation unit 5 determines the electrical conductivity κ from the admittance $Y_m$, as stated above. In contrast to the previously described embodiments, the conductivity sensor 1 shown in FIG. 11 implements a conductive-inductive measuring principle.

Figure 12:
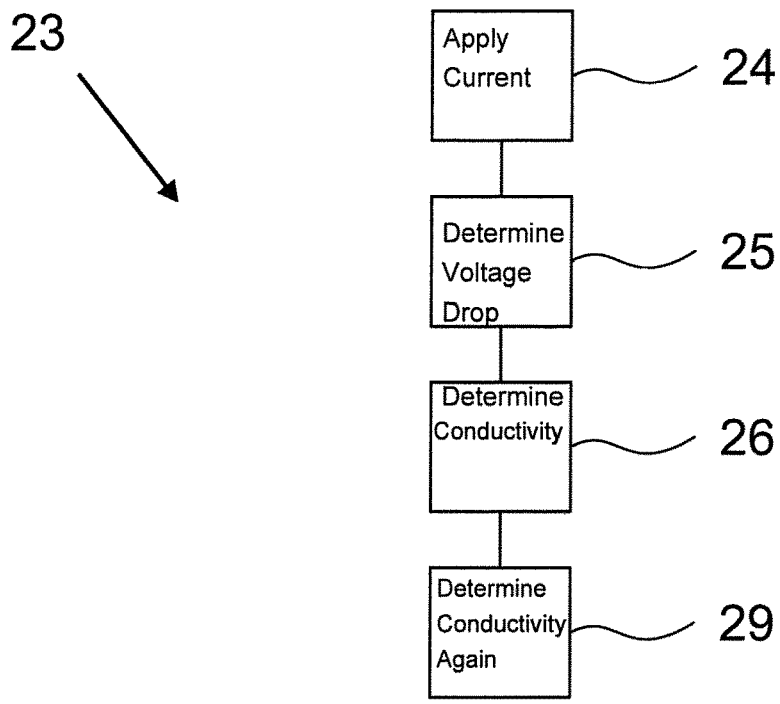
FIG. 12 is flow chart of a first embodiment of a method according to the invention.

FIG. 12 shows a first embodiment of a method 23 according to the invention for determining the electrical conductivity κ of a liquid medium 6 by means of a conductivity sensor 1 shown above, which implements an inductive-conductive method. In a first step 24, an alternating current is applied to the first coil 11. This produces a temporally changing magnetic flux density B, which induces an electric vortex field in the liquid 6. In a next step 25, the voltage drop across the liquid 6 is determined via the first electrode 2 and via the second electrode 3. After transferring the measured values to the control and evaluation unit 5, the latter determines the electrical conductivity κ of the liquid from the admittance $Y_m$ in a further step 26. In a last step 29, a second measurement of the electrical conductivity κ takes place by means of a conductive or inductive method, whereby the first measurement is verified.

Figure 13:
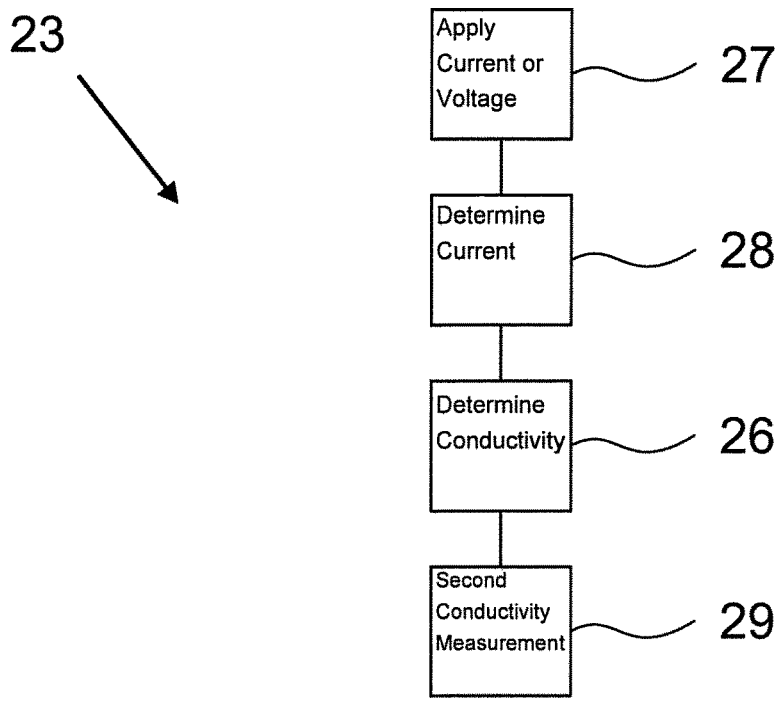
FIG. 13 is flow chart of a second embodiment of a method according to the invention.

FIG. 13 shows a second embodiment of a method 23 according to the invention for determining the electrical conductivity κ of a liquid medium 6 by means of a conductivity sensor 1 shown above, which implements a conductive-inductive method. In a first step 27, an alternating current or an alternating voltage is applied to the first electrode 2 and to the second electrode 3. As a result, an electric field is formed in the liquid 6, which generates a changing magnetic flux density B in the first coil 11. In a next step 28, the resulting current is determined by the first coil 11 and then the electrical conductivity κ is determined from the admittance $Y_m$ by the control and evaluation unit 5. In a next step 29, a second measurement of the electrical conductivity κ takes place by means of a conductive or inductive method, whereby the first measurement is verified.

The embodiments of the methods 23 according to the invention shown in FIGS. 12 and 13 are particularly suitable for determining a large value range of the conductivity κ and in particular for verifying mean values.

What is claimed is:

1. A conductivity sensor for measuring the electrical conductivity of a liquid medium comprising:
   at least a first coil,
   a current source connected to the first coil,
   a control and evaluation unit,
   at least a first electrode and a second electrode, and
   at least one voltage measuring unit, the voltage measuring unit being connected to the first electrode and the second electrode,
   wherein the control and evaluation unit is connected to the current source and to the at least one voltage measuring unit,
   wherein the first electrode and the second electrode are arranged out of electrical contact with the first coil, and
   wherein at least one electrically insulating unit is provided, the electrically insulating unit having an inner space and an outer space, the inner space being open,
   wherein the first coil surrounds the electrically insulating unit and the first coil and the first electrode and the second electrode are arranged parallel to one another along the electrically insulating unit.

2. The conductivity sensor according to claim 1, wherein the first coil is arranged between the first electrode and the second electrode.

3. The conductivity sensor according to claim 1, wherein the first electrode and the second electrode are arranged in the inner space on an inner side of the electrically insulating unit.

4. The conductivity sensor according to claim 1, wherein the first coil is arranged between the first electrode and the second electrode.

5. The conductivity sensor according to claim 1, wherein the first electrode and the second electrode are each arranged at one end of the electrically insulating unit.

6. The conductivity sensor according to claim 1, wherein the first electrode and the second electrode are arranged on the same side of the first coil.

7. The conductivity sensor according to claim 1, wherein an electrically conductive shield is arranged on at least one side of the first coil to avoid coupling between the first coil and at least one of the first and second electrodes.

8. The conductivity sensor according to claim 1, further comprising at least a second coil, the second coil being connected in parallel or series relative to the first coil.

9. A conductivity sensor for measuring the electrical conductivity of a liquid medium comprising:
   at least a first electrode and a second electrode,
   at least a current or voltage source, the current or voltage source being connected to the first electrode and the second electrode, and
   a control and evaluation unit,
   wherein at least a first coil and a current measuring unit are provided, the current measuring unit being connected to the first coil,
   wherein the control and evaluation unit is connected to the current or voltage source and to the current measuring unit,
   wherein the first electrode and the second electrode are arranged out of electrical contact with the first coil, and
   wherein at least one electrically insulating unit is provided, the electrically insulating unit having an inner space and an outer space, the inner space being open,
   wherein the first coil surrounds the electrically insulating unit and the first coil and the first electrode and the second electrode are arranged parallel to one another along the electrically insulating unit.

10. The conductivity sensor according to claim 9, wherein an electrically conductive shield is arranged on at least one side of the first coil to avoid coupling between the first coil and at least one of the first and second electrodes.

11. The conductivity sensor according to claim 9, wherein the first electrode and the second electrode are arranged in the inner space on an inner side of the electrically insulating unit.

12. The conductivity sensor according to claim 9, further comprising at least a second coil, the second coil being connected in parallel or series relative to the first coil.

13. The conductivity sensor according to claim 9, wherein the first electrode and the second electrode are each arranged at one end of the electrically insulating unit.

14. The conductivity sensor according to claim 9, wherein the first electrode and the second electrode are arranged on the same side of the first coil.

15. Method for determining the electrical conductivity of a liquid medium by means of a conductivity sensor arranged in the liquid medium, the conductivity sensor having at least a first coil, a current source and a control and evaluation unit, the current source being connected to the first coil, at least a first electrode and a second electrode and a voltage measuring unit, the voltage measuring unit being connected to the first electrode and the second electrode and the control and evaluation unit being connected to the current source and to the voltage measuring unit, the first electrode and the second electrode being out of electrical contact with the first coil, and the first electrode and the second electrode being in contact with one another via the liquid medium, wherein at least one electrically insulating unit is provided, the electrically insulating unit having an inner space and an outer space, the inner space being open, wherein the first coil surrounds the electrically insulating unit and the first coil and the first electrode and the second electrode are arranged parallel to one another along the electrically insulating unit, and the method comprises the following steps:

generating an alternating current in the first coil with the current source, whereby the first coil produces a temporally changing magnetic flux density which induces an electric field in the liquid medium, measuring the voltage between the first electrode and the second electrode with the voltage measuring unit, transferring values of the voltage and the current to the control and evaluation unit, and determining the electrical conductivity from the values of the voltage and the current with the control and evaluation unit.

16. Method according to claim 15, wherein the conductivity sensor comprises at least a second coil, the second coil has no connection with the first coil or is connected parallel or is in series to the first coil and determining the electrical conductivity is carried out both by means of the first coil and by means of the second coil, preferably the combination of the first coil and the second coil.

17. Method according to claim 15, wherein a current is applied to the first electrode and to the second electrode, and that the conductivity is determined conductively by the first electrode and the second electrode.

18. Method for determining the electrical conductivity of a liquid medium by means of a conductivity sensor arranged in the liquid medium, the conductivity sensor comprises at least a first electrode and a second electrode, at least a current or voltage source, and a control and evaluation unit, the current or voltage source being connected to the first electrode and to the second electrode, at least a first coil and a current measuring unit, the current measuring unit being connected to the first coil, the control and evaluation unit being connected to the current or voltage source and to the current measuring unit and the first electrode and the second electrode being arranged out of electrical contact with the first coil and the first and second electrodes being in contact with one another via the liquid medium, wherein at least one electrically insulating unit is provided, the electrically insulating unit having an inner space and an outer space, the inner space being open, wherein the first coil surrounds the electrically insulating unit and the first coil and the first electrode and the second electrode are arranged parallel to one another along the electrically insulating unit, the method comprising the following steps:

applying an alternating voltage or an alternating current to the first electrode and the second electrode with the current or voltage source, whereby a temporally changing electric field is introduced into the liquid medium, and a temporally changing magnetic flux density is induced in the first coil, measuring current flowing through the first coil with the current measuring unit, transmitting values of the voltage and the measured current to the control and evaluation unit, and determining the electrical conductivity from the values of the voltage and the current using the control and evaluation unit.

19. Method according to claim 18, wherein the conductivity sensor comprises at least a second coil, the second coil being connected with in parallel or series with the first coil, comprising the further step of determining the electrical conductivity both by means of the first coil and by means of the second coil.

20. Method according to claim 18, wherein a current is applied to the first electrode and to the second electrode, and wherein the conductivity is determined conductively by the first electrode and the second electrode.

\* \* \* \* \*